United States Patent [19]
Frosien et al.

[11] Patent Number: 6,093,512
[45] Date of Patent: Jul. 25, 2000

[54] METHOD AND APPARATUS FOR DIMENSION MEASUREMENT AND INSPECTION OF STRUCTURES UTILIZING CORPUSCULAR BEAM

[75] Inventors: Jürgen Frosien, Riemerling, Germany; Akira Kintaka, Saitama, Japan

[73] Assignee: Advantest Corporation, Tokyo, Japan

[21] Appl. No.: 09/189,832

[22] Filed: Nov. 10, 1998

[30] Foreign Application Priority Data

Jan. 23, 1998 [EP] European Pat. Off. .............. 98101206

[51] Int. Cl.⁷ ....................................................... G03F 9/00
[52] U.S. Cl. .............................. 430/30; 430/296; 382/145
[58] Field of Search ............................... 382/145; 430/30; 7/296

[56] References Cited

U.S. PATENT DOCUMENTS 5,741,614  4/1998  McCoy et al. ............................ 430/30

*Primary Examiner*—Christopher G. Young
*Attorney, Agent, or Firm*—Reising, Ethington, Barnes, Kisselle, Learman & McCulloch, P.C.

[57] ABSTRACT

The invention relates to a method and apparatus for dimension measurement and inspection of structures having a high aspect ratio, wherein a corpuscular beam is directed onto an interesting feature of the structure and backscattered corpuscles and/or secondary corpuscles released by the corpuscular beam are detected and evaluated. To increase the detection efficiency surroundings of the interesting feature are removed before measurement and inspection thereof.

17 Claims, 7 Drawing Sheets

METHOD AND APPARATUS FOR DIMENSION MEASUREMENT AND INSPECTION OF STRUCTURES UTILIZING CORPUSCULAR BEAM

The invention relates to a method and apparatus for dimension measurement and inspection of structures having a high height/width aspect ratio.

BACKGROUND OF THE INVENTION

To ensure both electrical performance and yield of highly integrated circuits, the integrated circuits have to be manufactured with high accuracy and reproducibility. This means that their geometrical dimensions, especially of transistors, lines and via holes, have to be kept within tight tolerances. With increasing integrated circuit integration and correspondingly decreasing feature sizes of the structures involved, tolerances have become narrower and extremely critical. To maintain electrical performance and yield, consequently, each process step in semi-conductor production has to be controlled by "Critical Dimension (CD) Measurement Tools" and "Inspection Microscopes". In the past, these tools were mainly light-optically based, such as a light-optical CD measurement system and a light-optical review station. At present, however, scanning electron microscopes are used to handle the small dimensions of the structures during their production. State of the art feature size is 0.25 $\mu$m and below, which requires a measurement accuracy of 20 nm and below, and the number of layers is increasing, i.e. 5 to 7 layers. Since such fine and multi-layer structures are "invisible" for light-optical equipment, scanning electron microscopes are now used for this purpose.

However, with decreasing structure sizes, even measurements based on scanning electron microscopes are reaching their limits. This limitation is not related to spatial resolution but to visibility and dimension measurement of structures with high aspect ratio. Semi-conductor technology requires a certain height of its structures (e.g. resist thickness, metal and oxide thickness). The aspect ratio (height/width of the structure) becomes increasingly larger. This especially applies to contact holes (via holes) having aspect ratios larger than 5 (0.2 $\mu$m hole in 1 $\mu$m resist layer).

Due to this high aspect ratio the visibility and accordingly the measurement of critical dimensions at the bottom of the structure, which is extremely important for the device characteristic, becomes difficult and in many cases impossible.

The reason for this invisibility is the secondary electrons released by the primary electron beam, which are difficult to detect. In post-lens detection systems, where the detector is arranged between the probe and the lens, the secondary electrons cannot be extracted from the bottom of the structure. In-lens or pre-lens detection systems, where the detector is arranged in or in front of the lens, use a high secondary electron attraction field causing the secondary electrons from the bottom of the structure to occupy only a small angle close to the optical axis and to move up the scanning electron microscope column in the direction of the cathode. Since the secondary electrons are extracted and accelerated, they behave very much like the primary electron beam and, therefore, are difficult to detect. Additionally, surface charging can influence the emission and detection of the secondary electrons.

The present solutions to overcome these problems are:
use of backscattered electrons for image generation,
positive surface charging of the upper part of the structure to extract the secondary electrons from the bottom of the structure,
use of a beam separator for the primary beam and secondary electron or backscattered electron beam, e.g. a Wien filter; this, however, requires an additional optical element in the microscope, which may influence the spatial resolution of the instrument.

Backscattered electrons and accelerated secondary electrons are, as mentioned, difficult to detect and require additional elements with consequent limitation of resolution. Artificial surface charging also causes disturbances of the primary beam and consequently causes measurement errors or limitations.

It is an object of the present invention to provide a method and an apparatus for dimension measurement and inspection of structures having a high aspect ratio, without limiting spatial resolution and without causing disturbances of the primary beam.

SUMMARY OF THE INVENTION

The invention is characterized in that surroundings of the interesting feature are removed before measurement and inspection thereof in order to increase the detection efficiency. Preferably, a corpuscular induced etching technique is used for the removal of the surroundings.

Before the removal of surroundings, an etching mask is generated which avoids damage to the interesting feature by covering it. In principal, there are two possibilities for increasing the detection efficiency:

1. At least parts of the material surrounding the structure are removed to a certain depth in order to decrease the aspect ratio.
2. An etching mask for the removal of the surroundings is generated, which avoids damage to the interesting feature and which overlaps the structure partially. The removal of the material will then open gateways for the backscattered and secondary corpuscles.

Further advantages and developments of the invention will be explained in greater detail by means of the description of the embodiments shown in the drawings.

THE DRAWINGS

FIG. 1 shows a schematic view of apparatus for dimension measurement and inspection of structures with a post-lens detection arrangement, FIG. 2 shows a schematic view of apparatus for dimension measurement and inspection of structures with a pre-lens detection arrangement, FIGS. 3a and 3b show a top view and a cross-section of a structure before applying the method according to the invention, FIG. 4 shows a schematic view of an etching mask for the structure according to FIGS. 3a and 3b, FIGS. 5a and 5b show a top view and a cross-section of the structure according to FIGS. 3a and 3b after removal of the surrounding material with the help of the etching mask according to FIG. 4, FIG. 6 shows a schematic view of an alternative etching mask, FIGS. 7a and 7b show a top view and a cross-section of the structure according to FIGS. 3a and 3b after removal of the surrounding material with the help of the etching mask according to FIG. 6, FIGS. 8a and 8b show a top view and a cross-section of another structure before applying the method according to the invention, FIG. 9 shows a top view according to FIG. 8a with an etching mask according to a third embodiment, FIGS. 10a and 10b show a cross-section of the structure according to FIGS. 8a and 8b indicating two different states when applying the method according to the invention, FIG. 10c shows a top view of the structure after the removal of surroundings.

FIG. 1 shows an apparatus for dimension measurement and inspection of a structure 1, with which a focused corpuscular beam 2, e.g. an electron beam or an ion beam, can be generated in an optical column 3.

DETAILED DESCRIPTION

Figure 1:
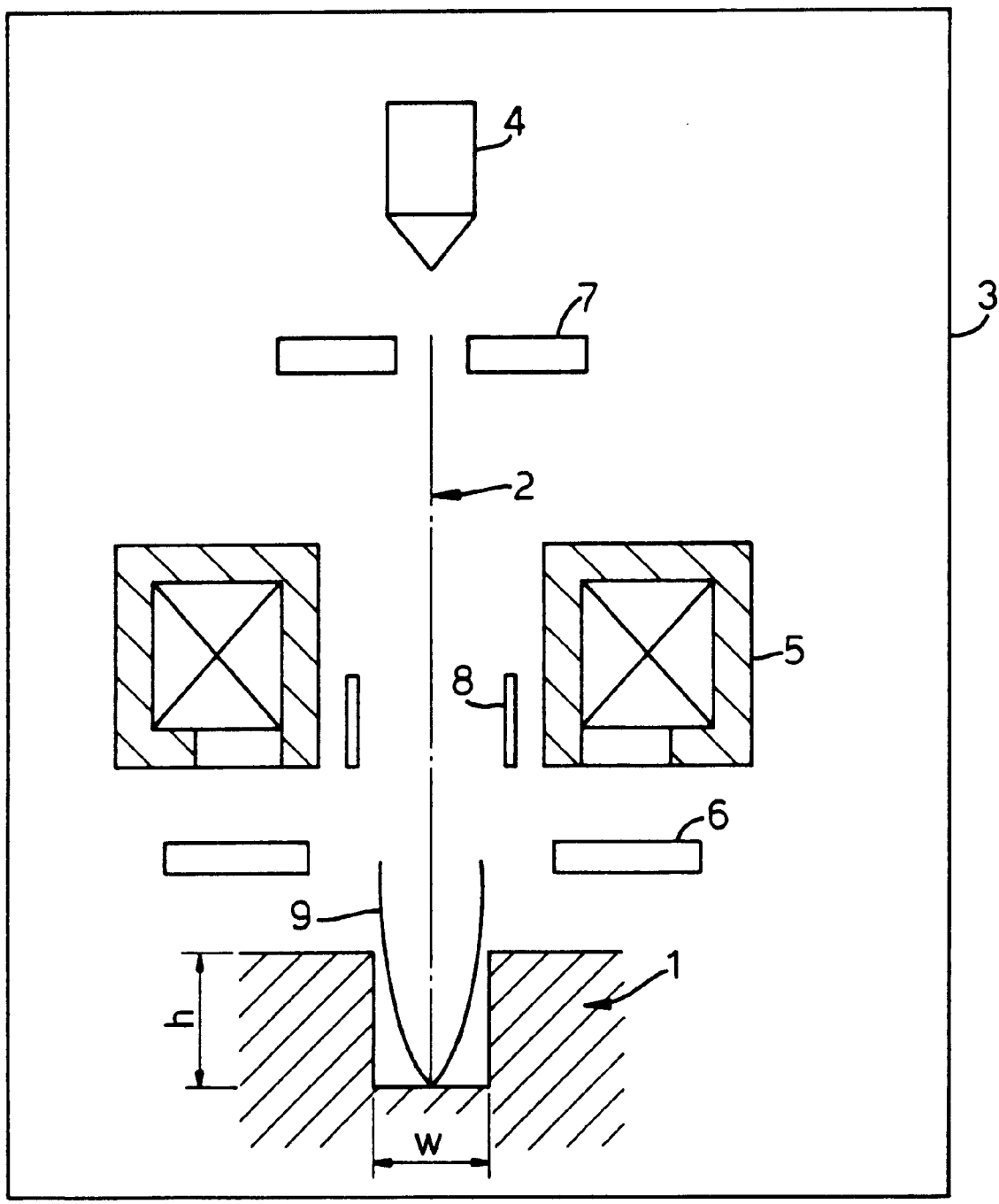

In addition to a plurality of magnetic and/or electrical lenses and diaphragms (not shown here) for beam formation, the column 3 essentially comprises means 4 for generating the corpuscular beam 2, an objective lens 5 for focusing the corpuscular beam onto the structure 1 and a detector 6 for detecting the backscattered electrons and/or the secondary electrons released by the focused corpuscular beam.

In the represented embodiment a blanking system 7 and a deflection system 8 are provided. The corpuscular beam 2 generated by the means 4 is focused on the structure 1 through the objective lens 5.

The backscattered and/or secondary electrons 9 released from the bottom of the structure 1 move upwards the optical column close to its optical axis and therefore, are difficult to detect by the detector 6.

Figure 2:
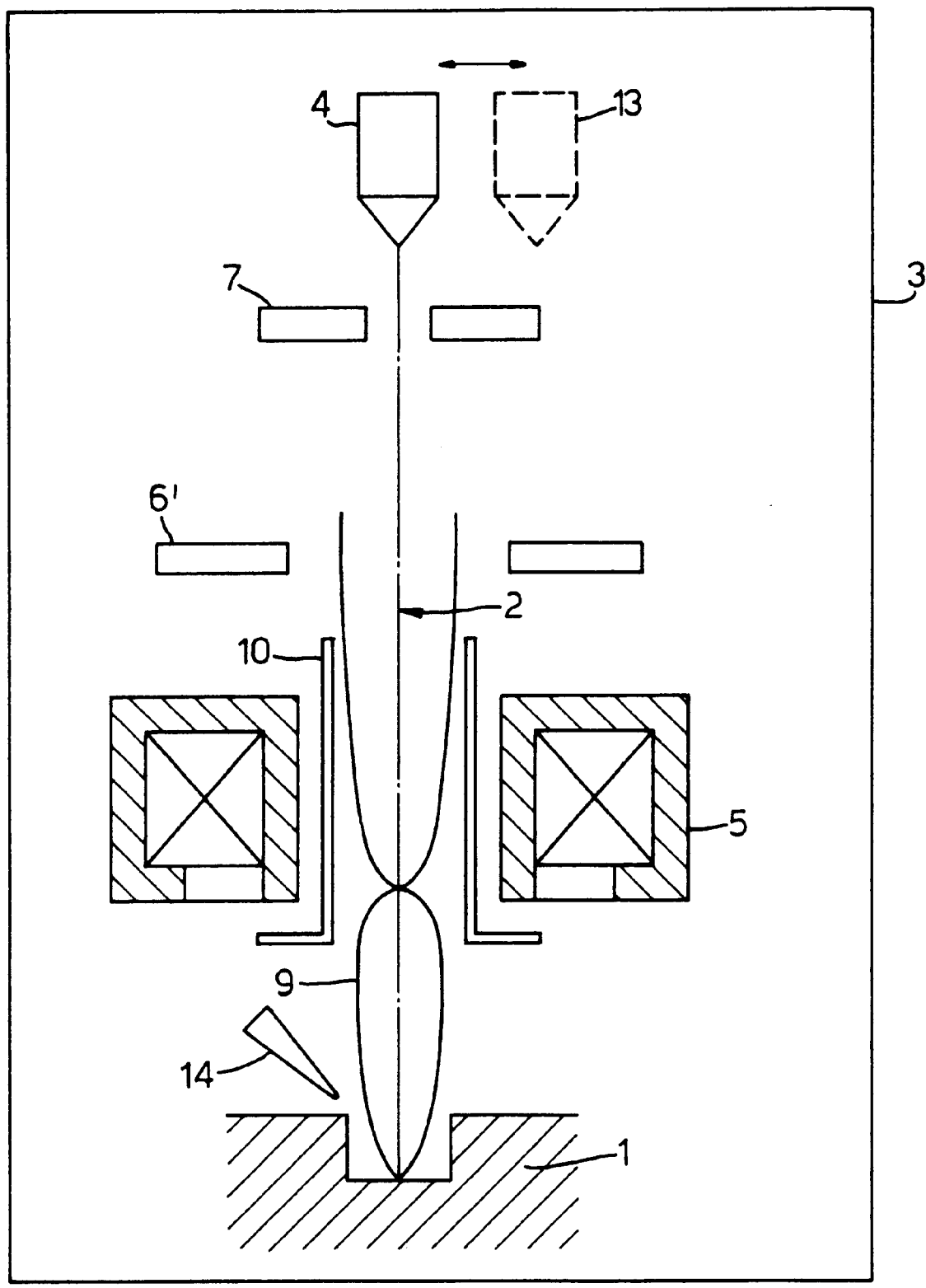

Apparatus for dimension measurement and inspection of structures having a high aspect ratio according to a second embodiment of the invention is illustrated in FIG. 2. While FIG. 1 shows a post-lens detection arrangement, FIG. 2 discloses a pre-lens detection arrangement. Accordingly, the detector 6' is arranged between the means 4 for generating the corpuscular beam and the objective lens 5. Furthermore, an acceleration electrode 10 is provided to help the backscattered and secondary electrons to pass through the objective lens 5. However, the accelerated backscattered and secondary electrons 9 then behave very much like the primary beam and therefore they are difficult to detect.

Figure 3A:
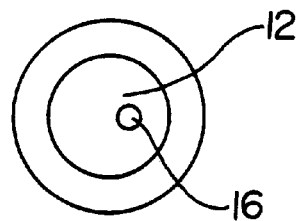
Figure 3B:
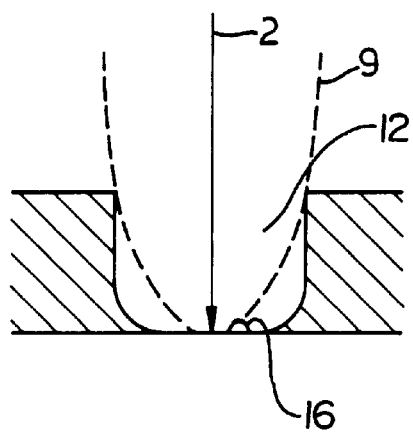

FIGS. 3a and 3b show a structure representing a contact hole. The interesting feature of this structure is, for instance, the diameter at the bottom of this hole.

In order to increase the detection efficiency, the method according to the invention proposes to remove surroundings of the interesting feature before its measurement and inspection.

Figure 4:
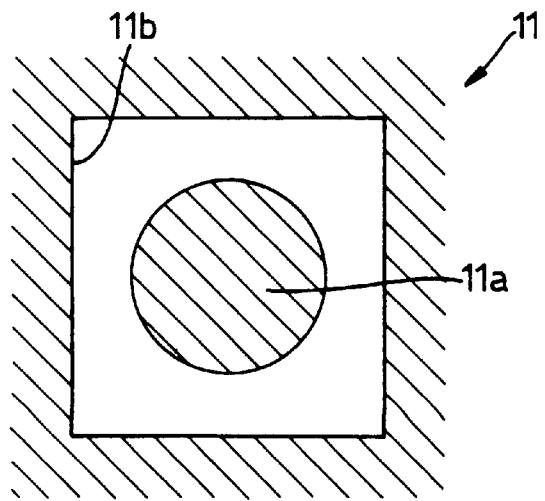

Before removal of surroundings, an image is advantageously made from the structure, e.g. by scanning it with the help of the corpuscular beam 2. From the top image data the etching mask is generated virtually. Then a virtual etching mask for the removal of the surroundings is generated which avoids damage to the interesting feature. A first example of an etching mask 11 for the structure according to FIGS. 3a and 3b is illustrated in FIG. 4. The etching mask comprises a round element 11a which has the same diameter as the contact hole 12 of the structure. Furthermore, the mask 11 defines a rectangular window 11b surrounding the round element 11a.

The apparatus according to FIG. 1 or FIG. 2 further comprises means for removal of surroundings of the interesting feature to increase the detection efficiency. These means can be defined by means 4 for generating the corpuscular beam. However, another possibility is to provide an additional means 13 for removal of surroundings of the interesting feature which are placed within the optical column 3.

Preferably, a corpuscular induced etching technique is used for the removal of the surroundings. For this purpose an ion beam or an electron beam can be used. Additionally, the means for removal of the surroundings can also comprise means 14 for supplying a gas in the region of the structure 1 to assist the beam in removing the surroundings. Therefore, it is possible to use a gas-assisted ion beam or a gas-assisted electron beam or even a gas-assisted light beam for the removal of the surroundings.

Preferably, the same corpuscular beam is used for the measurement and inspection as well as for the removal of the surroundings. However, an additional source 13 within or outside the optical column 3 can also be applied.

By applying a corpuscular induced etching technique, the mask 11 avoids damage to the interesting feature and restricts the area in which the material is to be removed.

Figure 5A:
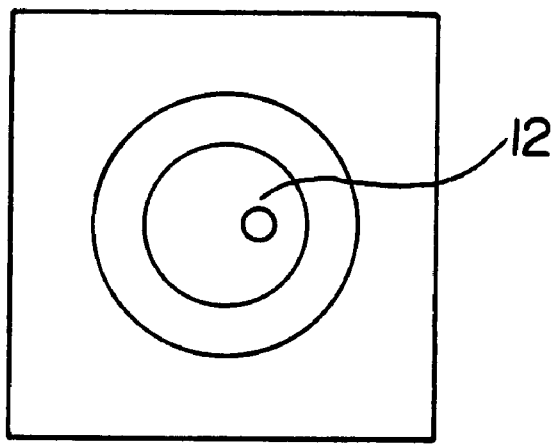
Figure 5B:
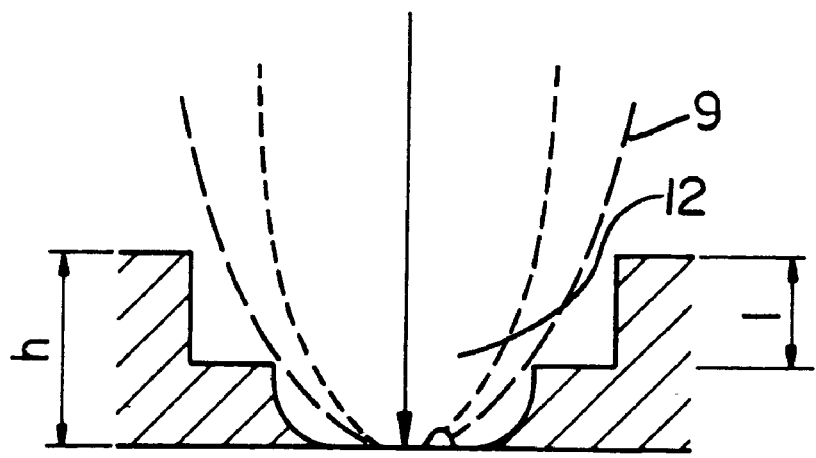

FIGS. 5a and 5b show the structure according to FIGS. 3a and 3b after the removal of the surroundings. The surroundings were removed to a certain depth l, thereby decreasing the aspect ratio. The removal of the surroundings enables the escape of the secondary electrons and backscattered electrons or other corpuscles as can be seen by FIG. 5b in comparison with FIG. 3b. Consequently, the imaging and high-precision critical dimension measurement is improved.

Figure 6:
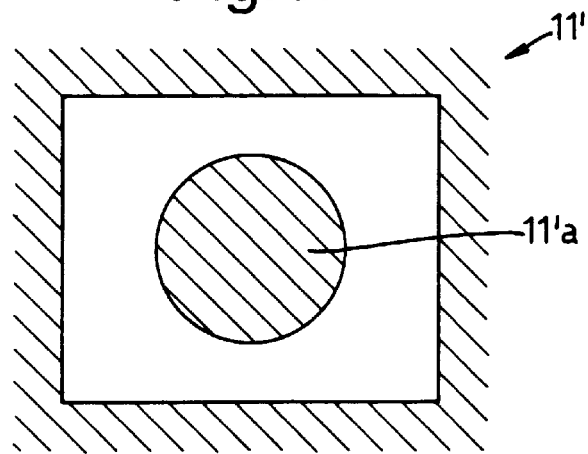
Figure 7A:
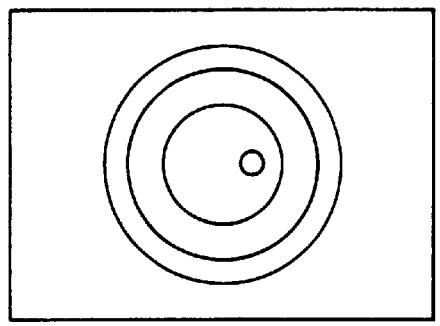
Figure 7B:
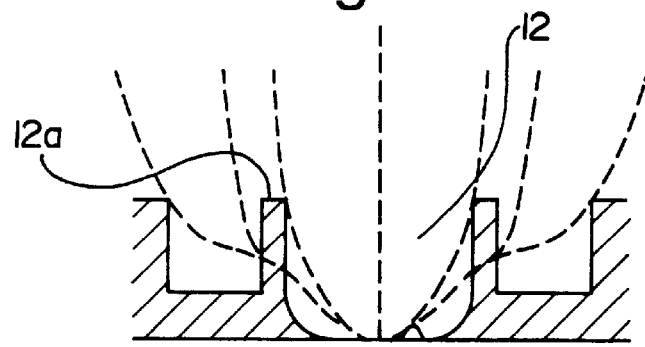

The etching mask according to FIG. 4, however, can also be made slightly larger than the structure in order to avoid damage to the interesting feature. FIG. 6 discloses such an etching mask 11'. Its round element 11'a has a diameter which is slightly larger than the inner diameter of the contact hole 12. In this case, a thin cylindrical wall 12a surrounding the feature is the result of the removal of the surroundings. Using such a solution, the secondary electrons generated by the backscattered electrons at the outer wall of the cylinder are used for signal detection in addition to the secondary electrons which can escape directly.

Figure 8A:
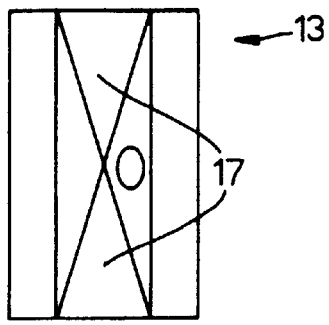
Figure 8B:
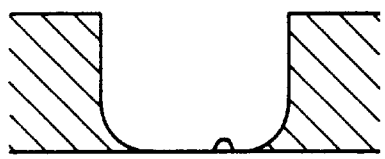
Figure 9:
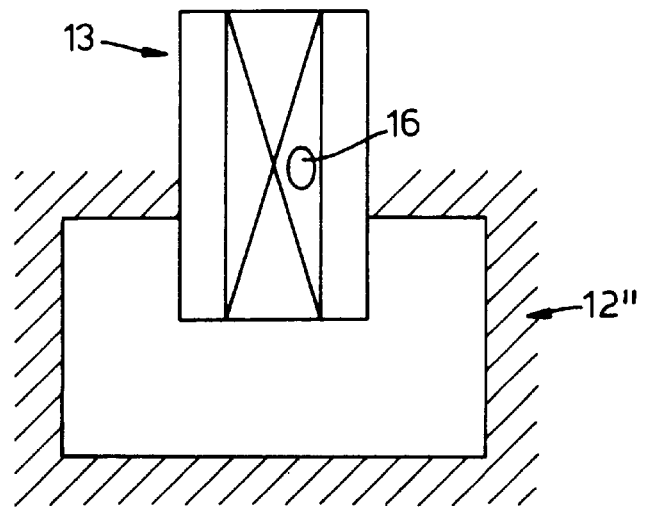

FIGS. 8a and 8b disclose another structure 13 which is to be inspected. This structure defines a thin groove.

In FIGS. 9 and 10a to 10c a novel technique for improving the detection efficiency is illustrated. Again an etching mask 12" is generated which avoids damage to an interesting feature 16. The etching mask 12" defines a rectangular window which partially overlaps the structure 13.

Figure 10A:
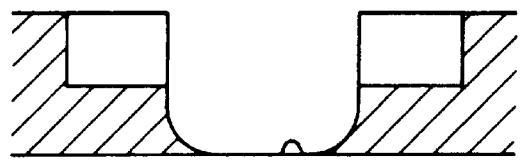
Figure 10B:
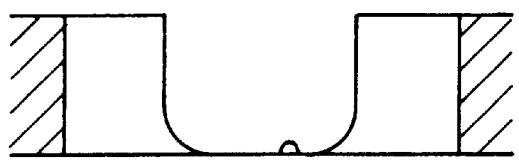

In the next step, the material is removed to a certain depth, e.g. half the depth of the groove as shown in FIG. 10a or the full depth of the groove as shown in FIG. 10b.

Figure 10C:
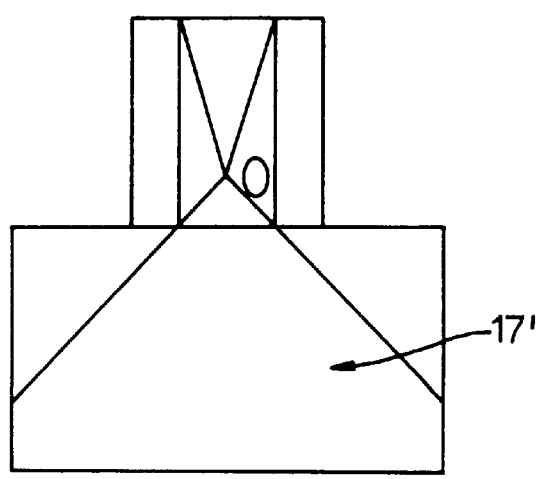

FIG. 10c is a top view of the structure after the removal of surrounding material which was defined by the mask 12". This technique opens the groove on one of its sides and, therefore, opens gateways for the backscattered and secondary corpuscles. FIG. 8a discloses an angular area 17 of corpuscle detection which is limited by the structure. Due to the removal of the surroundings, FIG. 10c shows an improved angular area 17' of corpuscle detection.

In some cases it may be advantageous to have a depth of the removed material which exceeds the depth of the structure.

The proposed methods and apparatus can be fully automated. Consequently, the critical dimension measurement and inspection can be undertaken without operator support. Known techniques like automatic navigation to measurement location, automatic setting of focus and beam parameter and automatic image acquisition can be used. From the resulting data the critical dimension data and the condition of the top layer can be determined using state of the art technology. Additionally the etching mask can be generated automatically from the top image data. Use of layout data can support this step. However, in some cases it may be preferable to generate the etching mask manually.

The generation of the etching mask and the removal of the material can be performed and controlled either by system parameter pre-settings or by using the contrast of the secondary and/or backscattered corpuscle signal. Preferably, secondary electron and/or backscattered electron signals will be used, but also secondary and/or backscattered ion signals are possible.

Usually, the etching masks will be generated virtually, and consequently, means 4 for generating the corpuscular beam and the blanking system 7 are supplied with control signals to generate a corpuscular beam on the structure corresponding to the etching mask.

To perform the method according to the invention an apparatus according to FIG. 1 or FIG. 2 can be used. A high-resolution (low-energy) secondary electron microscope is preferred having means 4 for generating an electron beam which is defined by a cold, thermal or photocathode electron source. The apparatus preferably has a blanking system 7 for electron dose control. Also components to increase spatial resolution and/or increase probe current such as aberration correction elements (e.g. multipole corrector), monochromators, can preferably be integrated.

Furthermore, a high-resolution focused ion beam apparatus having a liquid metal ion, a gaseous or another high-brightness ion source can be used. Finally, it is also possible to have a combination of a secondary electron microscope and a focused ion beam apparatus according to the above-mentioned features.

The apparatus should preferably have means for carrying out gas-assisted material removal techniques, e.g. one or more nozzles 14 for supplying suitable gases close to the corpuscular beam (cf. FIG. 2).

The number of etching masks to increase signal detection will depend on feature shape, measurement task and other requirements.

The orientation of the etching masks is selected according to the position of the detector or detectors to obtain maximum signal detection efficiency.

The orientation of the etching masks may also be chosen in such a way that optimum contrast effects (e.g. for special topography details) can be generated.

We claim:

1. Method for dimension measurement and inspection of structures having a high aspect ratio, wherein a corpuscular beam is directed onto an interesting feature of the structure and backscattered corpuscles and/or secondary corpuscles released by the corpuscular beam are detected and evaluated, characterized in that surroundings of the interesting feature are removed before measurement and inspection thereof to increase the detection efficiency.

2. Method according to claim 1, characterized in that a corpuscular induced etching technique is used for the removal of the surroundings.

3. Method according to claim 1, characterized in that a corpuscular induced etching technique is used for the removal of the surroundings and an etching mask for the removal of the surroundings is generated which avoids damage to the interesting feature.

4. Method according to claim 3, characterized in that an etching mask for the removal of the surroundings is generated which avoids damage to the interesting feature, the etching mask being generated manually.

5. Method according to claim 3, characterized in that an etching mask for the removal of the surroundings is generated which avoids damage to the interesting feature, the etching mask being generated automatically by first scanning an area including the structure.

6. Method according to claim 1, characterized in that the surroundings of the interesting feature are removed to a certain depth in order to decrease the aspect ratio.

7. Method according to claim 1, characterized in that an etching mask for the removal of the surroundings is generated which avoids damage to the interesting feature and which partially overlaps the structure in order to open gateways for the backscattered and secondary corpuscles.

8. Method according to claim 1, characterized in that an etching mask for the removal of the surroundings is generated which avoids damage to the interesting feature, the orientation of the etching mask being selected according to the position of the detector.

9. Method according to claim 1, characterized in that an ion beam is used for the removal of the surroundings.

10. Method according to claim 1, characterized in that a gas-assisted ion beam is used for the removal of the surroundings.

11. Method according to claim 1, characterized in that a gas-assisted electron beam is used for the removal of the surroundings.

12. Method according to claim 1, characterized in that a gas-assisted light beam is used for the removal of the surroundings.

13. Method according to claim 1, characterized in that the same corpuscular beam is used for the removal of the surroundings.

14. Apparatus for dimension measurement and inspection of structures having a high aspect ratio comprising means for generating a corpuscular beeam to be directed onto an interesting feature of the structure, detector means for detecting backscattered corpuscles and/or secondary corpuscles released by the corpuscular beam, characterized by means for removal of surroundings of the interesting feature to increase the detection efficiency.

15. Apparatus according to claim 14, characterized in that a means for generating an etching mask is provided.

16. Apparatus according to claim 14, characterized in that the means for removal of surroundings comprise means for generating a corpuscular beam and means for supplying a gas in the region of the corpuscular beam.

17. Apparatus according to claim 14, characterized in that the means for removal of surroundings comprise means for generating a virtual etching mask.

* * * * *